United States Patent [19]

Lindenberg et al.

[11] Patent Number: 5,518,498
[45] Date of Patent: May 21, 1996

[54] STENT SET

[75] Inventors: Josef Lindenberg; Wolfram Schnepp-Pesch, both of Karlsruhe, Germany

[73] Assignee: Angiomed AG, Karlsruhe, Germany

[21] Appl. No.: 132,929

[22] Filed: Oct. 7, 1993

[30] Foreign Application Priority Data

Oct. 9, 1992 [DE] Germany .............................. 9213656 U

[51] Int. Cl.⁶ ...................................................... A61F 2/02
[52] U.S. Cl. ...................................... 600/30; 128/DIG. 25
[58] Field of Search ...................... 128/DIG. 25; 600/29, 600/30; 606/191, 193, 194–199, 108; 604/104–105, 280–281

[56] References Cited

U.S. PATENT DOCUMENTS

| | | | |
|---|---|---|---|
| 3,797,478 | 3/1974 | Walsh et al. ............................ | 600/29 |
| 3,812,841 | 5/1974 | Isaacson ........................... | 128/DIG. 25 |
| 4,699,611 | 10/1987 | Bowden ................................. | 606/191 |
| 4,973,301 | 11/1990 | Nissenkorn . | |
| 4,994,066 | 2/1991 | Voss ........................................ | 606/191 |
| 5,030,199 | 7/1991 | Barwick et al. ........................ | 600/29 |
| 5,269,802 | 12/1993 | Garber ................................... | 606/191 |
| 5,306,226 | 4/1994 | Salama .................................... | 600/29 |

FOREIGN PATENT DOCUMENTS

WO91/10467  7/1991  WIPO .

*Primary Examiner*—Angela D. Sykes
*Assistant Examiner*—John P. Lacyk
*Attorney, Agent, or Firm*—Antonelli, Terry, Stout & Kraus

[57] ABSTRACT

A stent set for keeping a urethral stenoses open, particularly in the vesical neck, for bladder drainage with an intraurethral catheter having a largely cylindrical basic body, with small baskets or cages at respective ends of the basic end an intraurethral insertion rail and a slide. At a rounded tip with at least one initial opening is provided at a proximal end of the intraurethral catheter.

22 Claims, 2 Drawing Sheets

STENT SET

FIELD OF THE INVENTION

The invention relates to a stent set for keeping urethral stenosis open, particularly in the region of the vesical neck for bladder drainage with an intraurethral catheter and having a largely cylindrical basic body with small baskets at the ends, having an insertion rail and a slide.

BACKGROUND OF THE INVENTION

Intraurethral catheters are used for the treatment of intravesical occlusions, such as e.g. vesical neck adenomas, urethral stenoses or prostatic cancers and constitute an advantageous alternative to a catheter with a bent end, which has to be introduced, extends through the entire urethra and projects therefrom into the bladder, if the patient is on a waiting list or cannot or does not wish to undergo an operation. The intraurethral catheter is inserted in ambulatory manner under local anesthesia. Such cylindrical intraurethral catheters are slit in the end region and consequently have several uniform, expandable jacket portions provided in equivalent manner over the circumference and which are shaped to form a funnel or crown, through which the urine passes from the bladder for the discharge thereof into the internally constructed outflow channel. However, as a result of this construction incrustation can occur in the bladder, which subsequently lead to inflammation. Therefore such intraurethral catheters have to be constantly replaced.

An important disadvantage of the prior art is also that the slide for pushing the catheter out of the insertion rail must act on the catheter rear end, so that the catheter is compressed and consequently its wall, particularly in the vicinity of the baskets or cages, is pressed to a greater extent against the inner wall side of the insertion rail and ultimately the pushing out of the catheter is made very difficult.

SUMMARY OF THE INVENTION

The aim of the invention is to provide a stent set of the aforementioned type with an intraurethral catheter, insertion part, insertion rail and slide which, while avoiding the aforementioned disadvantages, permit a reliable insertion with little stress for the patient and the intraurethral catheter can remain permanently in the body.

With a stent set of the aforementioned type, according to the invention, at a proximal end, the intraurethral catheter has a rounded tip or point with at least one initial opening.

According to a first preferred embodiment, an initial opening is provided on the front of the rounded tip of the intraurethral catheter and generally the slide diameter is larger than that of the frontal initial opening.

Therefore, the invention has the important advantage that for the advance of the intraurethral catheter by the slide, action takes place on its front tip, which is closed or provided with an opening smaller than the cross-section of the slide, as opposed to on the rear end, as in the case in the prior art. As a result the catheter is "pulled" through the slide. It is therefore stretched during advance, expands somewhat and can easily and without significant friction be removed from the preferably bent front end of its insertion rail. As opposed to this the prior art catheter is compressed, if it is pushed from its rear end out of the rail. As a result of the compression there is a slight expansion of the catheter, so that the friction between it and the rail is increased, which makes sliding out more difficult.

According to a preferred development at its proximal end the intraurethral catheter has further initial openings, which represent a connection with the outflow channel within the intraurethral catheter and through which, during the insertion process, urine immediately enters the outflow channel of said catheter and passes out at the distal end of the internally hollow insertion part, so that it is apparent from the outside that the bladder has been reached. This is possible because the intraurethral catheter inserted in the insertion rail cannot be completely inserted due to the insertion part located within the rail; therefore its rounded tip with the initial openings at the proximal end project from the insertion rail.

In addition, the flat edges of the insertion rail are made gentler by the rounded tip of the intraurethral catheter, so that the patient is not injured or stressed on introduction. According to further developments the intraurethral catheter is preferably made from highly flexible material, e.g. polyethylene or polyurethane. Therefore it is easy to draw the intraurethral catheter into the insertion rail, so that the radially expanded baskets can be easily compressed by said insertion rail. On passing out of the rail, when the latter has been retracted, the baskets can be automatically radially drawn up again as a result of the relief action. As the vessels are also not always stretched and have curvatures, the necessary flexibility is ensured by the material used.

According to a further development, the front end of the insertion rail is slightly inclined or angled against the extension direction of its main body and an angled or bent end region has a cylindrical shape, with the end region having a length of between 1 and 3 cm. The end region is preferably bent at an angle of 10° to 50° to the main extension direction of the main body of the insertion rail and consequently has an obtuse angle between 130° and 170° thereto. The radius of curvature does not exist over the entire length and instead only occurs in a very short curvature range of which bending takes place by the desired angle and to which is connected a stretched end region with a length of 1 to 3 cm and which is oriented under the desired angle with respect to the main body. The insertion rail is made from a relatively stiff material, so that the bent end region remains slightly bent and cannot be drawn up through a slide made from highly flexible, but axially relatively stiff material and an intraurethral catheter also made from highly flexible material, when the slide and catheter are located within the insertion rail. However, the end region can be controlled during the insertion process, in that the insertion rail is slightly rotated. Therefore, the insertion rail engaged in spill-proof manner on the insertion part can be reliable guided by paths having bends.

Thus, the invention provides a stent set, which is not only controllable due to its bent end region by rotating the guide rail, but which allows an easy, reliable insertion of an intraurethral catheter into the intended area and can remain permanently in the body interior due to its design without infections arising due to incrustation.

BRIEF DESCRIPTION OF THE DRAWINGS

Further advantages and features of the invention can be gathered from the claims and following description of an embodiment of the invention with reference to the attached drawings, wherein:

DETAILED DESCRIPTION

Figure 1:
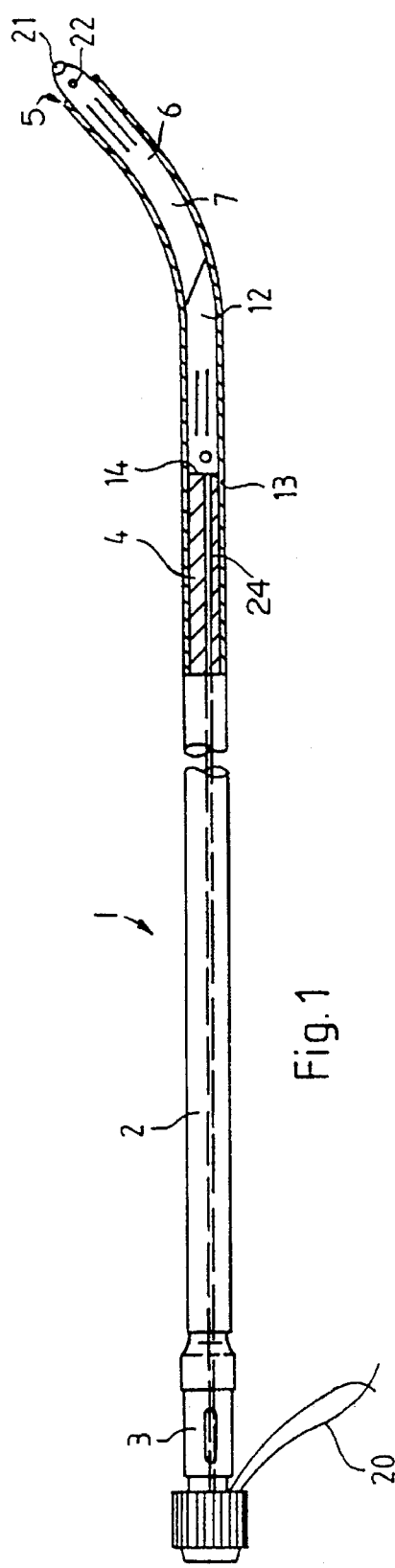
FIG. 1 is a partial cross-sectional view of a stent set according to the invention.

The stent set 1 according to the invention includes a hollow insertion rail 2, which is provided at its front or proximal end 5, i.e. pointing towards the body center after insertion, with a bent curvature area 7, to which is connected a short stretched end region 6. The end region 6 forms, with respect to the main body of the hollow insertion rail 2 an obtuse angle of 130° to 170°. In the hollow insertion rail 2 there is an intraurethral catheter 12 adapted to be introduced into a patient's body. The guide part 4 has a length such that when guide part 4 is completely engaged in the hollow insertion rail 2 and with the intraurethral catheter 12 inserted in the hollow insertion rail 1, the catheter 12 abuts with a cylindrical read end 13 thereof against a front end 14 of the guide part 4, whereas, a rounded tip 15 of the intraurethral catheter 12 projects out of the proximal end 5 of the guide part 4.

Figure 3:
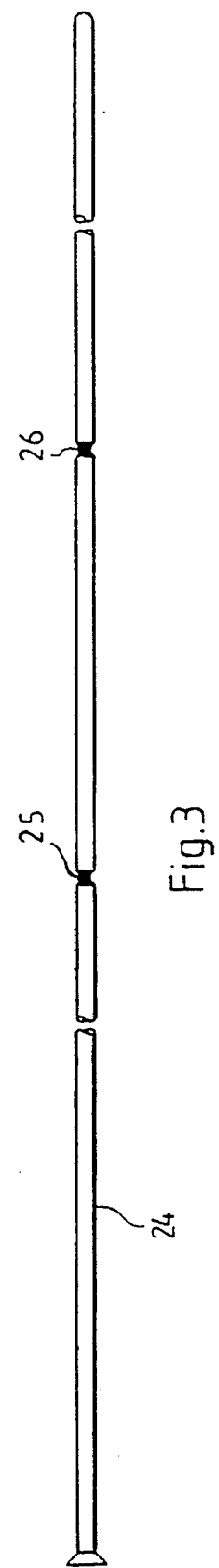
FIG. 3 is a plan view of a slide of the stent set according to the invention.
Figure 4:
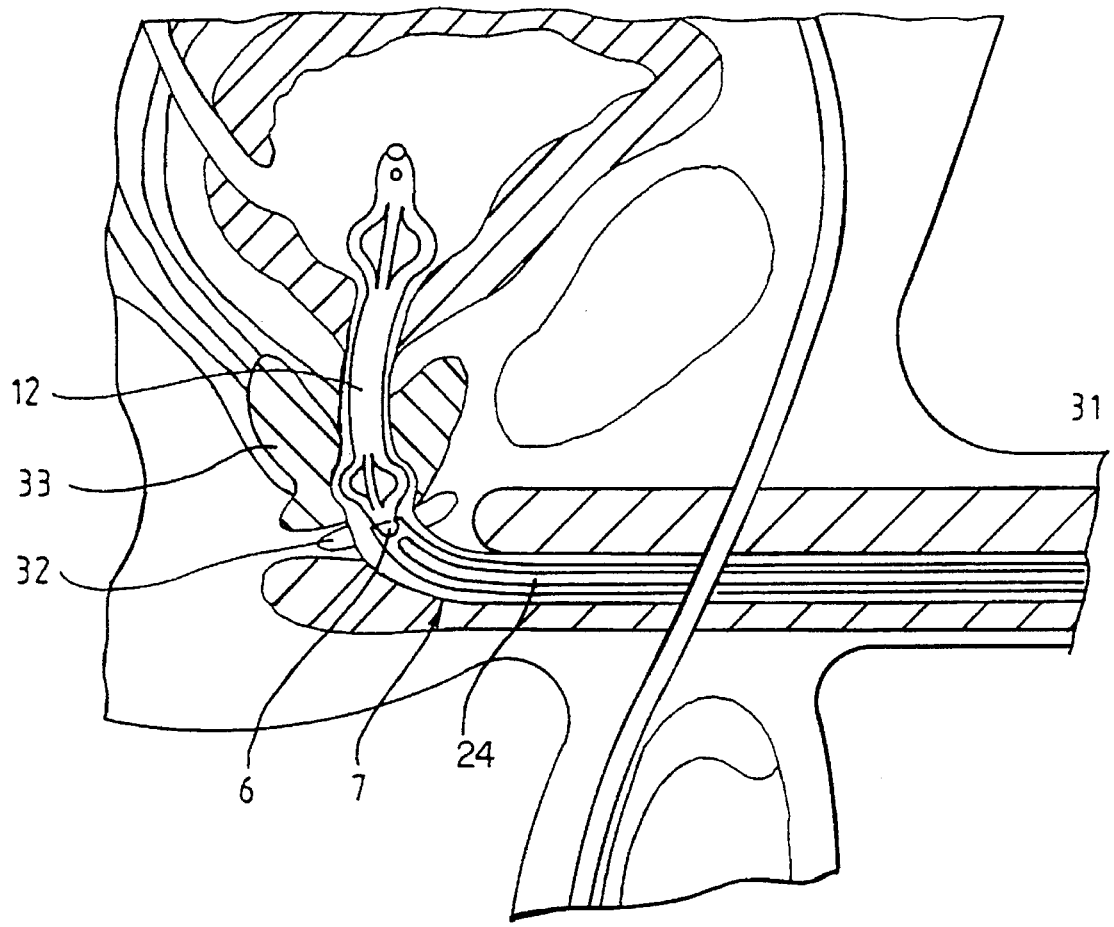
FIG. 4 is a cross-sectional view of a front curvature of an insertion rail of a stent set according to the present invention.

The guide part 4 may include a rear gripping part 3, for enabling inserting a slide 24 (FIG. 3) in the intraurethral catheter 12. The guide part 4 serves as a stop or slide-in limitation for the intraurethral catheter 12, so that during the advance of the hollow insertion rail 2, the intraurethral catheter 12 is not moved back further into the hollow insertion rail 2. The slide 24 which, completely inserted in the hollow insertion rail 2, in the guide part 4 and the intraurethral catheter 12, abuts from the inside against the rounded tip 15 of the catheter 12.

Figure 2:
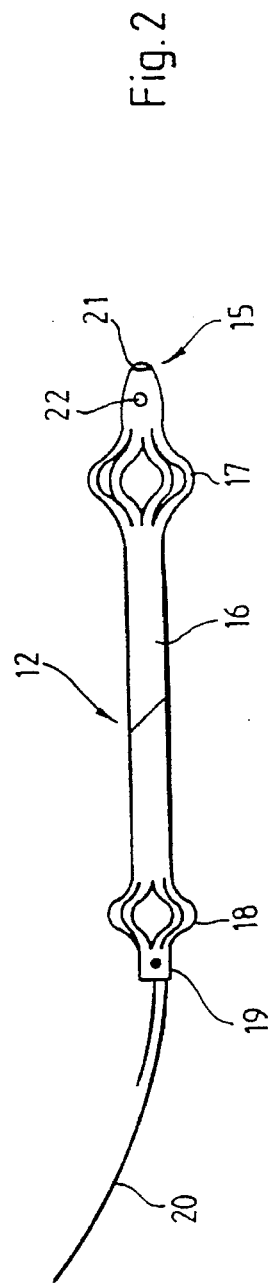
FIG. 2 is a schematic view of an intraurethral catheter of the stent set according to the invention.

The highly elastic, preferably polyethylene or polyurethane intraurethral catheter 12 shown in FIG. 2 has a cylindrical basic body with one small basket or cage 18, 17 respectively provided at the proximal and distal ends and an elongated part 16 of fixed length between the baskets 18, 17. The baskets 18, 17 are constructed in one piece with the elongated part 16 and above the basket 17, at the proximal end, the rounded tip 15 is connected in one-piece manner to the basket 17, while below the basket 18, at its side remote from the rounded tip 15, there is a cylindrical rear end part 13 connected in one piece thereto. The baskets 18, 17 are formed by providing longitudinal slots in the body of the intraurethral catheter 12, compressing the intraurethral catheter 12, so that the remaining ribs in this area are directed outwards, and fixing the intraurethral catheter 12 in this position by heat treatment. The intraurethral catheter 12 can have a different color on the distal half from a color on the proximal half.

The cylindrical end part 13 has an upper end face and a lateral opening 19 for receiving a thread 20 (FIG. 2). The thread 20, passed through the opening 19, is preferably a double thread, with ends of the thread 20 being knotted together at the end remote from the intraurethral catheter 12. The length of the knotted double thread 20 is at least 1½ times the length of the guide rail 4 and guide part 2 (shoved together). The catheter 12 can be subsequently removed again by the thread. The basket 17 at the proximal end is larger than the basket 18 at the distal end.

The slide 24 (FIG. 3), preferably made from highly flexible but axially relatively stiff material, has two marks 25, 26 in the form of indentations, which have a different reflecting power.

At its front end, the intraurethral catheter 12 is provided with initial openings 21, 22 through which, following the passage of the intraurethral catheter 12 into the bladder, liquid passes into the hollow insertion rail 2, respectively guide part 4 and at the rear end passes out of the hollow insertion rail 2, so that the position of the intraurethral catheter 12 is indicated.

The intraurethral catheter 12 is inserted in a conventional manner through the urethra 31 by the hollow insertion rail 2. In the transition region to the sphincter 32 and the prostate 33, the urethra 31 has a curvature. The curvature region 6 of the hollow insertion rail 2 is adapted to this curvature. When the hollow insertion rail 2 has been inserted through the urethra 31, the slide 24 is moved from the distal end of the hollow insertion rail 2 into the tip 15 of the intraurethral catheter 12. This impact can be seen from the outside in that the first mark 26 just projects from the distal end of the hollow insertion rail 2 respectively the guide part 4. The intraurethral catheter 12 is moved out of the hollow insertion rail 2 by the slide 24, so that the first, front basket 17 is located in the bladder 34 and the rear basket 18 in the urethra 31 in a vicinity of the prostate 33, so that the sphincter 32, after removing the hollow insertion rail 2, is not damaged. When the first basket 17 has been completely moved out of the hollow insertion rail 2, this is indicated by the second mark 25. On reaching the bladder 34 on insertion, urine immediately passes out of the initial openings 21, 22, so that it is clear from the outside that this stage is reached. After passing out from the hollow insertion or guide rail 2 the baskets 17, 18 radially expand, so that urine enters through the openings between the jacket portions of the basket 17 and can pass out through the opening of the basket 18. After insertion has taken place the slide 24, hollow insertion rail 2 and optionally guide parts 4 are retracted and removed from the urethra 31. The thread 20 can remain on the intraurethral catheter 12 for removing the latter or it is cut off and removed when the intraurethral catheter 12 is left in the body interior, because otherwise it can constitute an infection source.

The intraurethral catheter 12 introduced by the stent set 1 according to the invention can now remain permanently in the body or can be removed if, e.g. due to an operation being performed, it is no longer required.

We claim:

1. A stent set for keeping a urethral stenoses open in a region of a vesical neck for bladder drainage, the stent set comprising an intraurethral catheter having a substantially cylindrical main body with first and second baskets at respective opposite ends thereof, an entry urethral catheter insertion rail, and slide for pushing the intraurethral catheter out of the insertion rail, wherein the intraurethral terminates in a rounded tip at a proximal end thereof, at least one initial opening is formed at end face of said rounded tip, said insertion rail has an internal diameter for accommodating an external diameter of a guide part for the slide which can be located in said insertion rail, and wherein a diameter of the slide is greater than a diameter of the at least one initial opening.

2. A stent set according to claim 1, wherein the intraurethral catheter is provided with at least one further initial opening disposed at a lateral position of the proximal end.

3. A stent set according to claim 1, wherein the first basket is provided at the a proximal end of the intraurethral catheter at a position below the rounded tip, the second basket is provided at a distal end of the intraurethral catheter above a cylindrical end part thereof, and wherein a diameter of said first basket is larger than a diameter of said second basket.

4. A stent set according to claim 3, wherein said first and second baskets are constructed in one piece with the cylindrical end part, and wherein said cylindrical end part and said rounded tip of the intraurethral catheter are connected in one piece.

5. A stent set according to claim 1, wherein the intraurethral catheter has, on a cylindrical end part thereof remote from the rounded tip, an opening for receiving a thread.

6. A stent set according to claim 1, wherein the intraurethral catheter is provide with flat edges on an end face of a cylindrical end part thereof remote from said rounded tip.

7. A stent set according to claim 1, wherein the insertion rail is bent slightly with respect to a direction of the main body at a front end thereof.

8. A stent set according to claim 7, wherein a front end region of the insertion rail is bent by 10°–50° from the a direction of the main body of the insertion rail.

9. A stent set according to claim 7, wherein a front end region of the insertion rail forms an angle of between 130°–170° with respect to the main body.

10. A stent set according to claim 7, wherein a short curvature region is connected to the main body, and wherein the short curvature region is connected to said front end which is in the form of an extended short end region.

11. A stent set according to claim 10, wherein the short end region is cylindrical.

12. A stent set according to claim 1, wherein the slide includes two axially spaced marks respectively fashioned as indentation, and wherein the marks are provided with a different reflecting power as compared with a reflecting power of a remainder of the slide.

13. A stent set according to claim 1, wherein the slide is at least 1½ time a length of the insertion rail.

14. A stent set according to claim 1, wherein the slide has a smaller external diameter than an internal diameter of the intraurethral catheter.

15. A stent set according to claim 1, wherein the slide has a smaller external diameter than an internal diameter of the guidepart.

16. A stent set according to claim 1, wherein the insertion rail is fashioned of a stiff material.

17. A stent set according to claim 1, wherein the intraurethral catheter is fashioned of a flexible material.

18. A stent set according to claim 1, wherein the slide is fashioned of a flexible axially stiff material.

19. A stent set according to claim 17, wherein the flexible material is one of polyethylene and polyurethane.

20. A stent set for keeping a urethral stenoses open in a region of a vesical neck for bladder drainage, the stent set comprising an intraurethral catheter having a substantially cylindrical main body with first and second baskets at respective opposite ends thereof, an intraurethral catheter insertion rail, and a slide for pushing the intraurethral catheter out of the insertion rail, wherein the intraurethral catheter terminates in a rounded tip at a proximal end thereof, at least one initial opening is formed at an end face of said rounded tip, and wherein the insertion rail has an internal diameter corresponding to an external diameter of a guide part for the slide.

21. A stent set for keeping a urethral stenoses open in a region of a vesical neck for bladder drainage the stent set comprising an intraurethral catheter having a substantially cylindrical main body with first and second baskets at respective opposite ends thereof, an intraurethral catheter insertion rail, and a slide for pushing the intraurethral catheter out of the insertion rail, wherein the intraurethral catheter terminates in a rounded tip at a proximal end thereof, at least one initial opening is formed at an end face of said rounded tip, and wherein the intraurethral catheter is introduced into the insertion rail such that a distal end of said catheter abuts against a proximal end of the insertion rail and the rounded tip projects from said proximal end of the insertion rail.

22. A stent set according to claim 21, wherein the intraurethral catheter has an external diameter corresponding to an internal diameter of the insertion rail.

\* \* \* \* \*